US006228993B1

(12) United States Patent
Konwinski

(10) Patent No.: US 6,228,993 B1
(45) Date of Patent: May 8, 2001

(54) SOY ISOFLAVONE CONCENTRATE PROCESS AND PRODUCT

(75) Inventor: Arthur H. Konwinski, Fort Wayne, IN (US)

(73) Assignee: Central Soya Company, Inc., Fort Wayne, IN (US)

( * ) Notice: Subject to any disclaimer, the term of this patent is extended or adjusted under 35 U.S.C. 154(b) by 0 days.

(21) Appl. No.: 09/169,896

(22) Filed: Oct. 12, 1998

(51) Int. Cl.⁷ .............. A23J 1/14; A61K 35/78; A61K 47/00; A23B 4/03; A01N 37/18
(52) U.S. Cl. .............. 530/378; 426/472; 426/44; 426/46; 514/2; 424/439
(58) Field of Search .............. 530/378; 426/472, 426/44, 46; 514/2; 424/439

(56) References Cited

U.S. PATENT DOCUMENTS

| | | | |
|---|---|---|---|
| 3,870,805 | 3/1975 | Hayes et al. | 426/656 |
| 4,264,509 | 4/1981 | Zilliken | 260/345.2 |
| 4,366,082 | 12/1982 | Zilliken | 435/125 |
| 4,390,559 | 6/1983 | Zilliken | 426/545 |
| 4,428,876 | 1/1984 | Zilliken | 260/123.5 |
| 5,141,746 | 8/1992 | Fleury et al. | 424/195.1 |
| 5,320,949 | 6/1994 | Shen et al. | 435/68.1 |
| 5,352,384 | 10/1994 | Shen et al. | 252/398 |
| 5,637,562 | 6/1997 | Shen et al. | 514/2 |
| 5,670,632 | 9/1997 | Chaihorsky | 536/8 |
| 5,679,806 | 10/1997 | Zheng | 549/403 |
| 5,702,752 | 12/1997 | Gugger et al. | 426/634 |
| 5,726,034 | 3/1998 | Bryan et al. | 435/68.1 |
| 5,763,389 | 6/1998 | Shen et al. | 514/2 |
| 5,792,503 | 8/1998 | Gugger et al. | 426/634 |
| 5,821,361 | 10/1998 | Waggle et al. | 536/128 |
| 5,827,682 | 10/1998 | Bryan et al. | 435/68.1 |
| 5,851,792 | 12/1998 | Shen et al. | 435/68.1 |
| 5,858,449 | 1/1999 | Crank et al. | 426/556 |
| 5,919,921 | 7/1999 | Waggle et al. | 536/128 |
| 5,932,221 | 11/1999 | Day | 424/195.1 |
| 5,936,069 | * 8/1999 | Johnson | 530/378 |
| 5,990,291 | 11/1999 | Waggle et al. | 536/8 |
| 5,994,508 | 11/1999 | Bryan et al. | 530/378 |
| 6,013,771 | 1/2000 | Shen et al. | 530/378 |
| 6,015,785 | 1/2000 | Shen et al. | 514/2 |
| 6,020,471 | 2/2000 | Johns | 536/8 |
| 6,033,714 | 3/2000 | Gugger et al. | 426/634 |
| 6,083,553 | 7/2000 | Waggle et al. | 426/629 |

OTHER PUBLICATIONS

Isoflavones and Their Conjugates in Soy Foods: Extraction Conditions and Analysis by HPLC—Mass Spectrometry; Barnes, Stephen et al.; J. Agric. Food Chem.; vol. 42, No. 11, pp. 2466–2474 (1994).

The Phytoestrogens, Isoflavones, in Soybean Foods in the American and Asian Diets; Barnes, Stephen et al.; unpublished observations; reprints available from Dr. Stephen Barnes, Department of Pharmacology, University of Alabama at Birmingham; sent to Central Soya Company in Jul. 1991.

Genistein, Daidzein, and Their β–Glycoside Conjugates: Antitumor Isoflavones in Soybeans from American and Asian Diets; Coward, Lori et al.; J. Agric. Food Chem.; vol. 41, No. 11, pp. 1961–1967 (1993).

CRC Critical Reviews in Food Science and Nutrition; vol. 27, Issue 4, p. 230 (1988).

Determination of Isoflavones in Soybean Flours, Proteins, Concentrates, and Isolates; Eldridge, Arthur C.; J. Agric. Food Chem.; vol. 30, No. 2, pp. 353–355 (1982).

Malonyl Isoflavone Clycosides in Soybean Seeds (Glycine max Merrill); Kudou, Shigemitsu et al.; Agric. Biol. Chem.; 55(9), 2227–2233 (1991).

Mass Balance Study of Isoflavones during Soybean Processing; Murphy, Patricia A.; J. Agric. Food Chem.; vol. 44, No. 8, pp. 2377–2383 (1996).

Genistin (an Isoflavone Glucoside) and Its Algucone, Genistein, from Soybeans; Walter, E.D.; The Journal of American Chemical Society; vol. 63, pp. 3273–3276 (Dec. 1941).

* cited by examiner

*Primary Examiner*—Jezia Riley
(74) *Attorney, Agent, or Firm*—Michael L. Fueling

(57) ABSTRACT

A novel process for making an isoflavone concentrate product from soybeans which includes diluting solubles from alcohol-extracted hexane-defatted soybean flakes to about 10% to about 30% solids, separating undissolved solids from the diluted soy solubles, pasteurizing the separated solids and drying the pasteurized solids to make a product having at least 8 times the isoflavone content of the flakes.

19 Claims, No Drawings

SOY ISOFLAVONE CONCENTRATE PROCESS AND PRODUCT

BACKGROUND OF THE INVENTION

This invention relates to a process for making an isoflavone concentrate product from soybeans. Isoflavones are a unique class of phytoestrogens—plant hormones—that naturally occur in soybeans.

It is anticipated that consumer demand for soy isoflavones will continue to grow. Scientists have demonstrated that isoflavones have the ability to inhibit cancer cell growth, and some researchers believe that isoflavones may contribute to soy's ability to lower blood-cholesterol levels.

The principal types of isoflavones found in soybeans are glucones (with sugars) and aglucones (without sugars). Glucones have the glucose molecule attached, and include genistin, daidzin and glycitin. Aglucones are isoflavones without the glucose molecule, and they include genistein, daidzein and glycitein.

The prior art teaches isolating genistin from hexane-extracted soybean flakes. Walter ("Genistin (an Isoflavone Glucoside) and Its Aglucone, Genistein, from Soybeans," *J. of Am. Chem. Soc.*, 63, 3273 (1941)) describes a method involving, among other steps, extracting the flakes with methanol, precipitating with acetone and recrystallizing with ethanol.

U.S. Pat. No. 5,141,746 (Fleury et al.) describes a method for preparing an impure extract of two specific isoflavones daidzin malonate and genistin malonate. Fleury describes a method involving, among other steps, mixing hexane-defatted ground soybeans with 80 percent (%) aqueous methanol, filtering and drying; adjusting pH multiple times with, among other chemicals, hydrochloric acid and sodium hydroxide, and extracting with an organic solvent, such as butanol.

U.S. Pat. No. 5,352,384 (Shen) describes making an aglucone enriched fiber. Shen describes solubilizing isoflavones from soy flour by, among other steps, forming a slurry with an extractant, such as sodium, potassium or calcium hydroxide, to adjust the pH to the proteins' isoelectric point of 6.7–9.7, and reacting the slurry with the enzyme beta-glucosidase.

The use of multiple acids/bases and organic solvents to extract isoflavones from soybeans makes it costly to commercially manufacture soy isoflavone products. The use of a number of materials to extract isoflavones, not only increases raw material, equipment and labor costs, but also creates significant safety and environmental concerns.

It is apparent that an efficient process for removing isoflavones from soybeans is needed. It also is apparent that a low-cost soy isoflavone concentrate (SIC) product is needed.

SUMMARY OF THE INVENTION

I discovered a novel process for manufacturing a novel SIC product. The isoflavone content by weight of the SIC product is 8 to 11 times that of soy flour, which typically has about 0.6% by weight isoflavones. More particularly, the SIC product contains at least 4% by weight isoflavones, 20–60% protein, with it typically being at least one-third protein, and a relatively low amount of fiber, with it typically being less than 5% fiber.

My process does not use other chemicals, such as, acetone, hydrochloric acid or sodium hydroxide, to manufacture the SIC product from soy solubles. Soy solubles are recovered from alcohol-extracted hexane-defatted soybean flakes. These solubles, sometimes called soy "molasses", are desolventized, such that they contain less than 0.5% alcohol, and typically are evaporated to 60% solids.

I learned that soy solubles, on average, contain 3.31 milligrams per gram (mg/g) genistin on a wet basis and have a total isoflavone content (i.e., daidzin, glycitin, genistin, mal-daidzin, mal-genistin, daidzein, glycitein, genistein and some unidentified isoflavones) of 8.96 mg/g on a wet basis as determined by high performance liquid chromatography (HPLC). I discovered that if the soy solubles are diluted with water to form a slurry and the undissolved solids are removed from the slurry to form a wet "cake", the cake contains a significantly concentrated amount of isoflavones.

I further discovered that if the soy solubles, which have about 20 mg/g isoflavones on a dry basis, are diluted with water to a certain percent solids and the undissolved solids a separated from the diluted solubles with a certain type of centrifuge that the isoflavone content of the solubles can be concentrated by at least 2 times. It was surprising and unexpected to learn that a product with such a high isoflavone content could be produced from the soy solubles without adjusting the solubles' pH with bases or extracting the solubles with another solvent.

DETAILED DESCRIPTION OF THE INVENTION

The steps of the subject invention are: 1) dehulling whole soybeans; 2) flaking the dehulled soybeans; 3) extracting soybean oil from the flaked soybeans with hexane, a solvent; 4) desolventizing the defatted soybean flakes without high heating or toasting to produce "white" flakes; 5) extracting the white flakes with aqueous alcohol; 6) recovering solubles from the extraction; 7) desolventizing (removing alcohol) from the soy solubles; 8) diluting the soy solubles with water to form a slurry; 9) separating the undissolved solids from the slurry to form a cake and 10) drying the wet cake. The general procedure for steps 1 through 3 is well described in the prior art. E.g., "Extraction of Oil from Soybeans," *J. Am. Oil Chem. Soc.*, 58, 157 (1981) and "Solvent Extraction of Soybeans," *J. Am. Oil Chem. Soc.*, 55, 754 (1978).

The first step is the dehulling process in which the soybean hulls are removed from the whole soybeans. The soybeans are carefully cleaned prior to dehulling to remove foreign matter, so that product will not be contaminated by color bodies. Soybeans also are normally cracked into about 6 to 8 pieces prior to dehulling.

The hull typically accounts for about 8% of the weight of the whole soybean. The dehulled soybean is about 10% water, 40% protein, 20% fat, with the remainder mainly being carbohydrates, fiber and minerals.

The second step involves the flaking process. Soybeans are conditioned prior to flaking by adjusting moisture and temperature to make the bean pieces sufficiently plastic. The conditioned bean pieces are passed through flaking rolls to form flakes about 0.01 to 0.012 inches (in) thick.

In the third step, the soybean flakes are defatted by contacting them with hexane to remove the soybean oil. Soybean oil is used in margarine, shortening and other food and products, and is a good source of lecithin, which has many useful applications as an emulsifier.

A detailed description of the general procedure for steps 4 through 7 is found in U.S. Pat. Nos. 3,365,440 (Circle et al.) and 5,097,017 (Konwinski). These steps generally involve the alcohol process for manufacturing soy protein concentrate (SPC). SPC has been described in commerce as a product containing not less than 70% protein (N×6.25). See A. K. Smith and S. J. Circle, Editors, "Soybeans: Chemistry and Technology, Volume I, Proteins," the AVI Publishing Co., 1973.

In step 4, the hexane-defatted soybean flakes are desolventized—hexane is removed—without toasting to produce white flakes. This is different than conventional soybean oil hexane processes where the flakes are toasted and used for animal feed. Instead of being further processed into SPC, the white flakes can be ground to make soy flour.

In step 5, the white flakes are extracted with 55–75%, typically 60%, by weight aqueous ethanol in a countercurrent (flake to solvent flow) extraction device—extractor. The alcohol to flake ratio is about 5 to 1.

The alcohol extraction removes carbohydrates, including oligosaccharides, from the white flakes which thereby increases the protein content of the material. A typical sample of soy molasses from the SPC alcohol process was found to contain 7.80, 128.50, 19.45 and 86.79 mg/g glucose, sucrose, raffinose and stachyose, respectively, on a wet basis. Soy molasses also typically contains 7–8% protein and 10% ash on a wet basis.

The description of steps 8 through 10 is summarized in the previous section. In the preferred embodiment of this invention, the diluting, separating, pasteurizing and drying steps are performed in a continuous process.

In step 8, the soy solubles are diluted with water to form a slurry. In a preferred embodiment of this invention, the solubles are diluted to about 10% to about 30%, most preferred 18%, solids, resulting in the slurry's pH being 5.5–6.

It also usually is necessary to provide some agitation or mixing to slurry the diluted solubles. One means for performing the mixing is a propeller-type agitator.

In step 9, the undissolved solids are removed from the slurry to form a wet cake. The undissolved solids could be removed by a number of physical separation means; however, centrifugation is the most efficient and effective means.

In the preferred embodiment of this invention, a scroll-type centrifuge is used to remove the undissolved solids from the slurry, such that wet cake is 25–30% solids and contains about 20% of the soy solubles' solids. In yet another embodiment of this invention, the separation can be performed with a disc-type or tubular centrifuge.

Alternatively, the dilution and separation steps 8 and 9 could be described as water "washing" the soy solubles. These steps serve to extract and concentrate the soy isoflavones from the solubles. In another embodiment of this invention, the washing process may be repeated one or more times in an effort to further concentrate the isoflavones, however, product yield (the quantity of SIC produced) would decrease.

In a preferred embodiment of this invention the wet cake is pasteurized prior to the drying step 10, so that the SIC will test negative for salmonella and have an acceptable microbial profile. One means for pasteurization is to hold the wet cake in a steam-jacketed kettle for 10 minutes at 160° F.

In step 10, the wet cake is dried to produce SIC useable as a nutritional supplement, or a food ingredient or product. The preferred means of drying is a vertical spray dryer with a high pressure nozzle. To facilitate spray drying, the wet cake is diluted to less than 25% solids, most preferred 15%, prior to pasteurization.

The spray-dried powdered SIC has many uses. For example, it can be tableted or used in drink mixes.

The spray-dried powdered SIC may be coated with commercial lecithin or other food-grade surfactants, such as mono-diglycerides, to improve water dispersibility and reduce clumping of the product. Such a coating-addition would be in the range of about 0.5%.

These examples illustrate the practice of this invention:

EXAMPLE 1

Solubles with 53.5% solids and 11.6 mg/g total isoflavones on a wet basis were recovered from alcohol-extracted hexane-defatted soybean flakes. The solids content of the solubles was adjusted to approximately 18%, and the resulting slurry was passed through a scroll-type centrifuge at a feed rate of 30 gallons per minute. The cake contained about 27% solids, and was diluted to about 18% solids. It was then pasteurized at 170° F., and spray dried at a rate of about 400 pounds (lbs) of dry solids per hour in a vertical spray dryer using pressure nozzles. The spray-dried product contained 6.1% total isoflavones.

EXAMPLE 2

Solubles with 55.9% solids were recovered from alcohol-extracted hexane-defatted white soybean flakes. 150 lbs of the solubles were mixed with 303 lbs of water with a propeller-type mixer to form a slurry of 453 lbs of material with 17.72% solids. The slurry was passed through a Sharples tubular bowl (Model AS-12) scroll-type centrifuge to form 23.35 lbs of cake with 35.5% solids. The cake was freeze-dried to produce a product with a total isoflavone content of 82.44 mg/g.

What is claimed:

1. A process for manufacturing a soy isoflavone concentrate product which comprises the steps of:
   (a) diluting desolventized solubles from alcohol-extracted hexane-defatted soybean flakes with water to about 10% to about 30% solids;
   (b) separating undissolved solids from said diluted solubles;
   (c) drying said separated solids to make a soy isoflavone concentrate product having at least 8 times the isoflavone content by weight of said flakes before alcohol extraction.

2. A composition comprising a soy isoflavone concentrate product produced in accordance with the process of claim 1, either alone or in combination with a nutritional supplement or food ingredient or product.

3. The process of claim 1 wherein the flakes contain about 0.6% by weight isoflavones before alcohol extraction.

4. The process of claim 1 wherein the alcohol is 55–75% by weight aqueous ethanol.

5. The process of claim 1 wherein the diluted solubles are 18% solids.

6. The process of claim 1 wherein the separating step is performed with at least one scroll-type centrifuge.

7. The process of claim 1 wherein the drying step is performed by spray drying.

8. The process of claim 7 further comprising diluting the separated solids to less than 25% solids prior to the pasteurizing step.

9. The process of claim 1 wherein the isoflavone content by weight of the soy isoflavone concentrate product is at least 4%.

10. A process for making a soy isoflavone concentrate which comprises the steps of:

(a) extracting white soybean flakes with alcohol;
(b) desolventizing solubles from said extracted flakes;
(c) diluting said desolventized solubles with water to about 10% to about 30% solids;
(d) separating undissolved solids from said diluted solubles;
(e) diluting said separated solids with water;
(f) pasteurizing said diluted solids;
(g) drying said pasteurized solids to form a soy isoflavone concentrate product having at least 8 times the isoflavone content by weight of said white flakes.

11. A composition comprising a soy isoflavone concentrate product produced in accordance with the process of claim 10, either alone or in combination with a nutritional supplement or food ingredient or product.

12. The process of claim 10 wherein the white flakes contain about 0.6% by weight isoflavones.

13. The process of claim 10 wherein the alcohol extraction is performed with 55–75% by weight aqueous ethanol in a countercurrent extractor.

14. The process of claim 10 wherein the diluted solubles are 18% solids.

15. The process of claim 10 further comprising separating undissolved solids from the diluted solids prior to the pasteurizing step.

16. The process of claim 10 wherein the separating step is performed with at least one scroll-type centrifuge.

17. The process of claim 10 wherein the diluted solids are less than 25% solids.

18. The process of claim 10 wherein the drying step is performed by spray drying.

19. A composition comprising a soy isoflavone concentrate product produced in accordance with the process of claim 18, either alone or in combination with a nutritional supplement or a food ingredient or product.

* * * * *

UNITED STATES PATENT AND TRADEMARK OFFICE
CERTIFICATE OF CORRECTION

PATENT NO.  : 6,228,993 B1
DATED       : May 8, 2001
INVENTOR(S) : Arthur H. Konwinski It is certified that error appears in the above-identified patent and that said Letters Patent is hereby corrected as shown below:

Claims,
Insert the following;
19. A continuous process for manufacturing a soy isoflavone concentrate product which comprises the steps of:

(a) providing desolventized solubles from alcohol-extracted hexane-defatted soybean flakes with said desolvenized solubles having about at least 50% solids with said solids containing undissolved isoflavones;

(b) diluting said desolventized solubles with water to about 10-30% solids;

(c) separating about at least 20% of said solids containing said undissolved isoflavones from said diluted solubles to form a wet cake;

(d) drying said cake to make a soy isoflavone concentrate product having an isoflavone content of about at least 5% by weight.

20. A composition comprising a soy isoflavone concentrate product produced in accordance with the process of claim 19, either alone or in combination with a nutitional supplement of food ingredient or product.

3. On the cover sheet, there should be a reference to Patentee's related U.S provisonal application in an item number [60]. The related provisional application as cited below was referenced in Patentee's Declaration. Patentee respectfully requests that the Patent Office issue the corrected patent with a reference to the related provisional application.

Provisional application no. 60/062,046, October 15, 1997.

4. On the patent cover sheet, there is a typographical error in the OTHER PUBLICATIONS section. In the sixth reference, entitled "Malony Isoflavone Clycosides in Soybean Seeds," Clycosides" (emphasis added) should be corrected to "Glycosides" as cited in the Invention Disclosure Statement. Patentee respectfully requests that the Patent Office make this spelling correction in the corrected patent requested.

5. On the patent cover sheet, in the Attorney section, "Fueling" should be corrected to "Fuelling" as typed into the Issue Fee Transmittal.Patentee respectfully requests that the Patent Office make this spelling correction in the corrected patent requsted.

Additionally, while the Examiner apparently did not consider the Second Substitute Specification, filed by Applicant on December 4, 2000, Patentee respectfully requests

UNITED STATES PATENT AND TRADEMARK OFFICE
CERTIFICATE OF CORRECTION

PATENT NO.    : 6,228,993 B1
DATED         : May 8, 2001
INVENTOR(S)   : Arthur H. Konwinski It is certified that error appears in the above-identified patent and that said Letters Patent is hereby corrected as shown below:

respectfully requested in that filing.

In dependent claim 8 of the issue patent, "the pasteurizing step" (emphasis added) probably should be "a pasteurizing step."

In independent claim 1 of the issued patent, it appears that there is an extra space between identifier (b) and the text. The same appears to be true for (d) and possibly (c) of independent claim 10.

Signed and Sealed this

Fifth Day of February, 2002

Attest:

Attesting Officer

JAMES E. ROGAN
Director of the United States Patent and Trademark Office